United States Patent
Fank

(10) Patent No.: US 8,631,731 B2
(45) Date of Patent: Jan. 21, 2014

(54) SAFETY HOLDER FOR A MICROTOME KNIFE

(75) Inventor: Reiner Fank, Rauenberg (DE)

(73) Assignee: Microm International GmbH, Walldorf (DE)

(*) Notice: Subject to any disclaimer, the term of this patent is extended or adjusted under 35 U.S.C. 154(b) by 875 days.

(21) Appl. No.: 12/656,860

(22) Filed: Feb. 18, 2010

(65) Prior Publication Data

US 2011/0030523 A1 Feb. 10, 2011

(30) Foreign Application Priority Data

Aug. 5, 2009 (DE) .......................... 10 2009 036 190

(51) Int. Cl.
*G01N 1/06* (2006.01)

(52) U.S. Cl.
USPC ................. 83/397; 83/713; 83/546; 83/915.5

(58) Field of Classification Search
USPC ............. 83/397, 915.5, 715, 546, 478, 440.2, 83/DIG. 1, 713
See application file for complete search history.

(56) References Cited

U.S. PATENT DOCUMENTS

| | | | | |
|---|---|---|---|---|
| 1,925,181 | A * | 9/1933 | Fassin ............................ | 83/433 |
| 3,527,133 | A * | 9/1970 | Imhof et al. ............... | 83/699.51 |
| 4,117,753 | A * | 10/1978 | Friddle et al. .................... | 83/143 |
| 5,161,446 | A * | 11/1992 | Holbl et al. ..................... | 83/703 |
| 5,851,213 | A * | 12/1998 | Berleth et al. ................ | 606/167 |
| 7,146,894 | B2 * | 12/2006 | Hendrick et al. ............... | 83/703 |
| 2001/0003938 | A1 | 6/2001 | Heid | |
| 2006/0219080 | A1 * | 10/2006 | Heid .............................. | 83/651 |

* cited by examiner

Primary Examiner — Laura M Lee
(74) Attorney, Agent, or Firm — Paul Vincent

(57) ABSTRACT

A knife holder device for a microtome having a blade guard constituted as a pivotable bow, wherein, in a protective position, the blade guard is disposed on the side of the knife facing away from the sample at a distance such that access to the cutting edge is not possible. The blade guard can be positioned in three different defined positions and is provided with elements that have the following effects depending on the position: in the upper, protective position, simultaneous fixing of the position of the knife holder in the guideway; in the central, knife-holder-sliding position, accessibility to the knife holder with simultaneous release of the position fixture of the knife holder in the guideway; and in the lower, knife-changing position, free accessibility to the knife holder with simultaneous fixture of the position of the knife holder in the guideway.

11 Claims, 7 Drawing Sheets

SAFETY HOLDER FOR A MICROTOME KNIFE

This application claims Paris Convention priority of DE 10 2009 036 190.1 filed Aug. 5, 2009 the complete disclosure of which is hereby incorporated by reference.

BACKGROUND OF THE INVENTION

The invention concerns a knife holder for a microtome having a blade guard constituted as a pivotable bow, wherein, in its protective position, the blade guard is disposed on the side of the knife facing away from the sample at a distance from the cutting edge of the knife such that access to the cutting edge is not possible, and wherein the knife holder is held in a guideway on a support element in such way that it can be laterally slid and fixed so as to deploy different regions of the cutting edge during the sectioning operation.

Microtomes are used to make thin sections of the most varied specimens in medicine, biology, material research, and quality control of technical substances in a thickness range from approx. 0.1 µM to 100 µm. Biological and medical specimens are frequently embedded in more solid materials (e.g. paraffin, synthetic resin) to provide the stability necessary for sectioning.

The sections are produced either as single sections or as continuous series of sections. Thin sections are prepared using knives of different shapes and attributes. The known types include steel knives made of selected tool steels that are manufactured by various grinding methods. In addition to these resharpenable solid knives, disposable blades are used that are classified into low-profile blades and high-profile blades and are replaced with new blades once they have exceeded their useful life (usefulness for sectioning). Glass knives and diamond knives are also used for special applications.

Depending on the type of microtome, the knife is either moved along a stationary specimen in a sled (classic sled microtome) or the specimen is moved along the stationary knife by means of a specimen sled (rotary microtome). Stationary means that the knife is completely fixed during the entire sectioning operation. Of course, the knife can be placed in different positions in front of the sample between cuts, as is required for approximate positioning of the knife in front of the sample, advancement of the knife during sectioning, and also for lateral movement of the knife to make use of the entire cutting region of the knife.

In the case of rotary microtomes, the knife is usually held firm by clamping into a knife holder, wherein the knife is placed against the base body of the knife holder in such a way that the cutting edge protrudes beyond this base body and is clamped firmly thereon by means of a clamping plate. This is usually achieved using a simple clamping lever that either fixes or releases the knife.

The knife holder is usually on a support element constituted as a segment arc that is used to adjust the angle at which the knife cuts through the sample. The segment arc is positioned with its arc-shaped underside in a correspondingly constituted depression in the base support below it, which is in a guideway in front of the specimen holder and permits movement toward and away from the sample. This enables the knife to be put into position and advanced.

To be able to adjust the lateral position of the knife with respect to the sample in order to deploy other regions of the cutting edge, a guideway on the segment arc is used in which the knife holder can be moved laterally with respect to the sample.

To secure the selected position of the knife for the sectioning operation, the knife holder must be fixed, which can be achieved, for example, by means of a clamping mechanism. Such a mechanism is usually a simple clamping lever that either fixes or releases the knife holder in its position in the guideway.

The primary purpose of the knife holders used is to clamp the knife stably, i.e. with as little vibration as possible, so as to achieve a thin section of the necessary quality, i.e. without damaging or distorting the tissue. An essential property of all knives used is that the cutting edge is sharp enough for the specimen to be sectioned and for the selected section thickness in order to achieve a clean initial cut followed by clean parting of the tissue. It is the task of the user to monitor the progress of sectioning, for which purpose a free view of the cutting edge in the region of the sample is necessary during sectioning. The section or series of sections produced is deposited over the cutting edge on the knife cutting edge or on the clamping plate of the knife holder, depending on the specimen size, and must be removed from there. This is achieved, for example, using a fine brush or a pair of tweezers.

For the user of the microtome, all handling of the device therefore involves a danger of incurring cut wounds to the hand. In the case of rotary microtomes with a stationary knife, blade guard mechanisms are usually provided that cover the cutting edge during preparatory work, in work breaks, or during idle times. For this purpose, these guard mechanisms are either freely placed onto the knife or they are fixed to the knife holder and can be slid or pivoted into their protective position. All these finger guard mechanisms have the disadvantage that they provide no protection during the work phase because they have to be removed from the cutting edge region for use, in particular, for removing the section from the knife.

DE 198 24 024 A1 discloses a knife holder that has a pivotable blade guard constituted as a plate, wherein, in the protective position, the plate is disposed on the side of the knife facing away from the sample at a distance from the cutting edge of the knife such that access to the cutting edge is not possible. This bow-like pivotable blade guard can extend over the entire length of the knife and does not need to be removed for section removal. When access to the knife holder is required, e.g. to change the knife or to reposition the knife holder laterally, the blade guard can be swung out of its working position into its inoperative position. Then free access to the knife holder and operation of the clamping mechanisms are possible.

The disadvantage of this device is that the blade guard must be swung into position in addition to operating the knife holder. During the routine work that is performed with a microtome, in particular, each unnecessary operation is inconvenient for the user because it interferes with his or her work flow. This can result in the user preferring not to use the blade guard at all and operating the microtome without putting the blade guard in its protective position, which invalidates the function of the blade guard to reduce the risk of injury. Because routine work, in particular, is only performed by semi-skilled operators who cannot adequately assess the danger posed without having been trained in and practiced the necessary skills, but who have to work under time pressure, this results in a special hazard for laboratory personnel.

The objective is therefore to further develop a knife holder with a blade guard of the type stated above such that operability is improved and simplified, while also adequately ensuring safe operation for less skilled personnel.

SUMMARY OF THE INVENTION

This is achieved for a knife holder of the type stated above in that the blade guard is constituted such that it can be positioned in three different positions and means are provided that have the following effects depending on the position:

a) in the upper, protective position, simultaneous fixture of the position of the knife holder in the guideway,
b) in the central, knife-holder-sliding position, accessibility to the knife holder with simultaneous release of the position fixture of the knife holder in the guideway,
c) in the lower knife-changing position, free accessibility to the knife holder with simultaneous fixture of the position of the knife holder in the guideway.

and that the blade guard and the means are constituted such that ergonomic removal of sections is only possible in the protective position.

Because positioning of the blade guard simultaneously controls fixture of the knife holder in its lateral position, the operator only has to operate one element (the blade guard) instead of two (blade guard and clamping lever). At the same time, this function coupling has the essential advantage that sectioning is only possible when the blade guard is swung into its protective position because ergonomic section removal is only possible in this position. In the knife-changing position, in which the knife holder is also fixed in its guideway, access by the hand during section removal is made more difficult by the swung-forward position of the bow of the blade guard so that the user is not really able to produce sections in this position. The user would have to adopt a tiring and uncomfortable arm posture for each section removal and could not deploy his or her hand optimally. In the knife-changing position, by contrast, trim sections can be prepared in which the coarse cuts are performed on the embedding material of the specimen until the actual sample or the layer thereof to be examined is reached. The waste off-cuts thereby produced either fall from the knife itself or can be removed without exercising great caution with respect to the sections, so that convenient access to the cutting edge region is not necessary.

Only when real sections are made is the sectioning operation performed with advancement of the knife to the required section thickness and careful removal of the sections from the knife or from the clamping plate is required because the sections are extremely sensitive to mechanical stresses. This requires convenient, i.e. ergonomically favorable intervention in the knife region. Because this is blocked to the user in the knife-changing position, the user can now no longer dispense with use of the blade guard out of convenience. Safe operation of the microtome is therefore ensured by purely mechanical means even in hectic work situations without the user having to be convinced of the safety benefits.

There are various ways of implementing these basic functions of the invention: for example, the blade guard could be positioned by manual pivoting, then detecting this with a sensor and fixing or releasing the knife holder in the guideway, for example, by mechanical or electromagnetic means.

However, in one especially advantageous embodiment of the means, the means comprise:

a) a bearing for receiving a shaft in the support element
b) a mechanical linkage between the blade guard and the shaft
c) a clamping element for fixing the knife holder while in the protective position and the knife-changing position, that interact in such a way that, while the blade guard is positioned in the protective position and in the knife-changing position, the clamping element fixes the position of the knife holder in its guideway and, in the knife-holder-sliding position of the blade guard, fixture of the knife holder is released. This direct mechanical coupling of the blade guard with means for fixing the position of the knife holder can be simply manufactured and permits reliable and largely low-wear and low-maintenance use.

In the further dependent claims, advantageous embodiments of the blade guard or the means are described.

In an advantageous embodiment of the mechanical means, the shaft comprises both a support region and an eccentric region with two eccentric clamping keys that are constituted by the shaft having a flat section in the eccentric region in a partial region of its circumference, wherein the transitions from the circumference to the flat section constitute the eccentric clamping keys and the clamping element has an essentially T-shaped head part for engagement in a correspondingly shaped slot on the underside of the knife holder and thereunder a hole for receiving the shaft with an engagement region in the lower part of the hole, and the clamping element is disposed perpendicularly with respect to the bearing and passes through the bearing in the eccentric region so that the hole is largely aligned with the bearing and the head part, protruding from the support element, engages in the slot on the underside of the knife holder in such a way that, when one of the eccentric clamping keys engages with the engagement region of the clamping element, the latter is moved downward and fixes the knife holder in its guideway by clamping due to the action of the head part in the slot of the knife holder, which corresponds to the protective position and the knife-changing position of the blade guard. By contrast, the positioning of the flat section in the engagement area corresponds to the knife-holder-sliding position of the blade guard in which the fixture of the knife holder is released. This permits implementation with the least effort possible as compared with prior designs. Only the shaft, which, on conventional devices, is used by the knife holder clamping lever to fix the knife holder, and the bow of the blade guard are affected by this, so that the invention can easily be retrofitted even to existing devices.

In an advantageous further embodiment, the shaft has a recess, and a latching element is constituted and disposed in such a way that it latches into the recess during positioning of the blade guard in position W. In this way, reliable positioning of the blade guard in the central knife-sliding position can be achieved. The user can feel that the latching element has engaged during the pivoting movement and therefore knows that the correct position has been set. Moreover, latching has the effect that this position is held with only minor forces but further pivoting is not prevented.

The latching element can, for example, be constituted by a spring with a ball mounted in this spring, wherein the ball then latches into the recess of the shaft. The flexibility of the spring permits easy handling.

Moreover, it is advantageous if the shaft comprises a ring slot and an engaging element is provided that is constituted and disposed in such a way that it engages in this slot, thus securing the shaft (8) against unwanted displacement in the bearing. This ensures the correct position of the shaft with respect to the other active elements during use.

In one possible embodiment, the shaft comprises a first part and a second part and both parts of the shaft are connected to the blade guard via a mechanical linkage and are disposed in the bearing, wherein the eccentric region is disposed in the first part of the shaft. This makes it easier to manufacture the eccentric part but it also makes assembly easier. Both parts of the shaft are introduced into the bearing from their respective sides. The bearing can be constituted to be continuous or correspond to the length of the shaft parts.

In an advantageous embodiment, the blade guard has a flat section toward the side facing away from the sample that is dimensioned and disposed such that the user has a free view of the cutting edge of the knife in the protective position. This enables an improved view by the user of the sample the cutting edge, and the sections to be removed while retaining the protection function. This flat section can adapted to the angle of viewing.

In a further advantageous embodiment of the blade guard, the blade guard has a projection on the side of the user's hand as an operating lever for the user's hand. This facilitates operation. The projection must be constituted such that it can be conveniently gripped with one or two fingers and still exert good leverage, in particular, with the thumb and index finger. The projection can, for example, be constituted by an arch extending outward or a protruding tab, e.g. by a flat section of the otherwise round cross-section of the bow.

If the blade guard is constituted as a single component, the blade guard can be made stable against torsional forces during operation.

In a possible further embodiment of the blade guard, the blade guard comprises a limiting element disposed laterally inside the bow of the blade guard that, in the protective position, is located to the left and/or right of the knife holder so that a lateral limitation is set for positioning of the knife holder in its guideway during the sectioning operation. This can ensure, if necessary, that the knife holder can only be positioned within a predetermined range within the guideway.

The invention is explained by means of drawings. The figures show

DESCRIPTION OF THE PREFERRED EMBODIMENT

Figure 1:
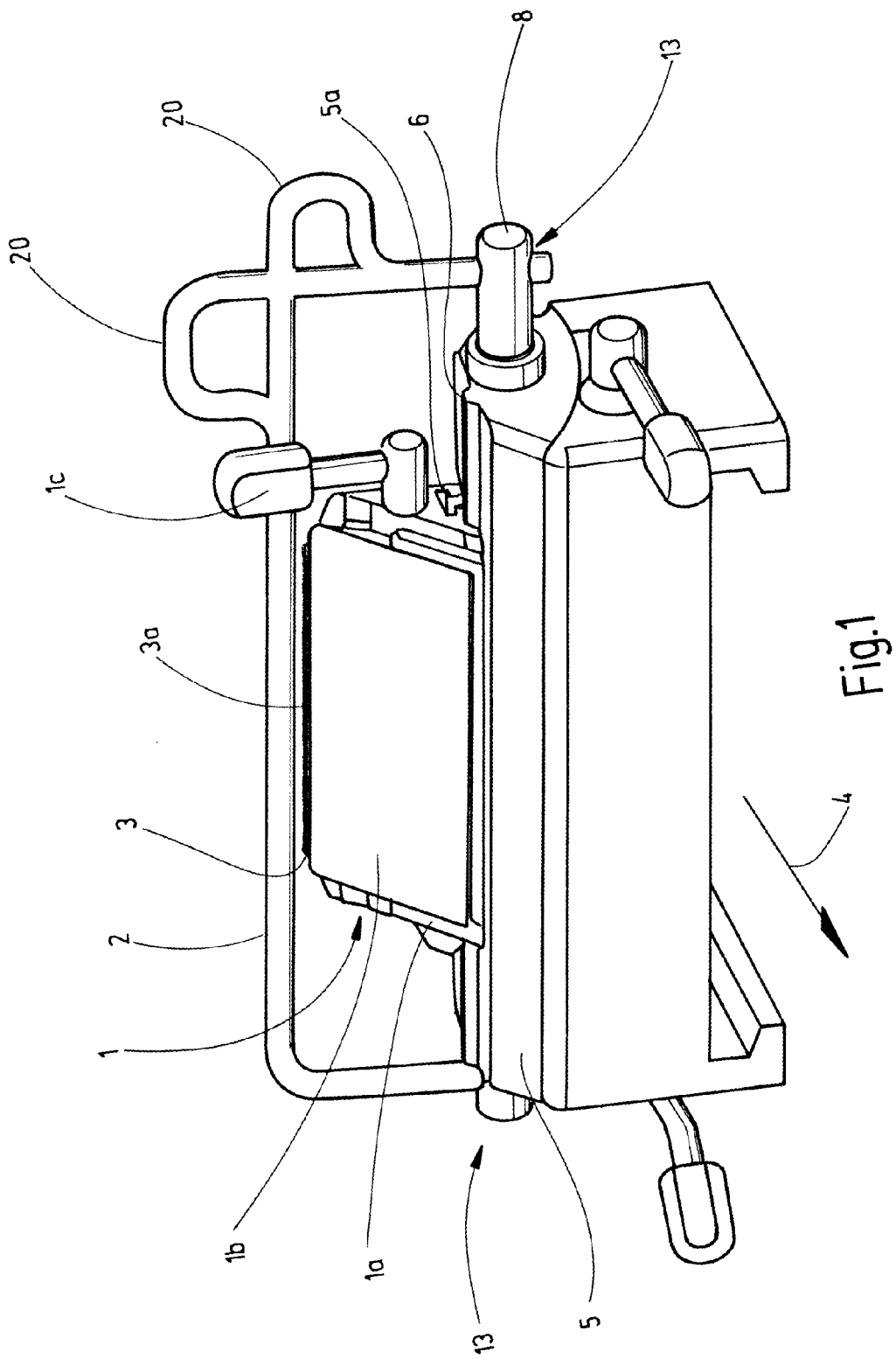
FIG. 1 an inventive knife holder with a blade guard in a perspective view.

FIG. 1 shows an inventive knife holder 1 with the blade guard 2 on the support element 5 constituted as a segment arc and located in the depression of the base support (without reference symbol). A knife 3 is clamped on the base body 1a of the knife holder 1 by means of the clamping plate 1b and the clamping lever 1c. Only the cutting edge 3a protrudes upwardly out of the knife holder 1. The sample is guided along in an object sled (not shown) behind the knife 3, i.e. the side 4 of the knife 3 facing away from the sample is on the observer's side.

The knife holder 1 is guided in the guideway 6 of the segment arc 5 in such a way that lateral adjustment of the knife holder 1 and therefore use of all regions of the cutting edge 3a of the knife 3 is possible because the samples to be cut only take up a small part (usually in the mm to cm range) of the width of the cutting edge 3a. A shaft 8 that is connected to the blade guard 2 via a mechanical linkage 13 extends through the segment arc 5 so that, on a pivoting movement of the blade guard 2, the shaft 8 performs the same pivoting movement. In the drawing, the blade guard 2 is in the protective position S, i.e. the bow of the blade guard 2 extends in front of the cutting edge 3a above and parallel with the latter so that contact with the user's hand or fingers is prevented.

The blade guard 2 has two projections 20 that can improve operability. These projection shapes are only two of the possible variations that can be used individually or combined.

Figure 2:
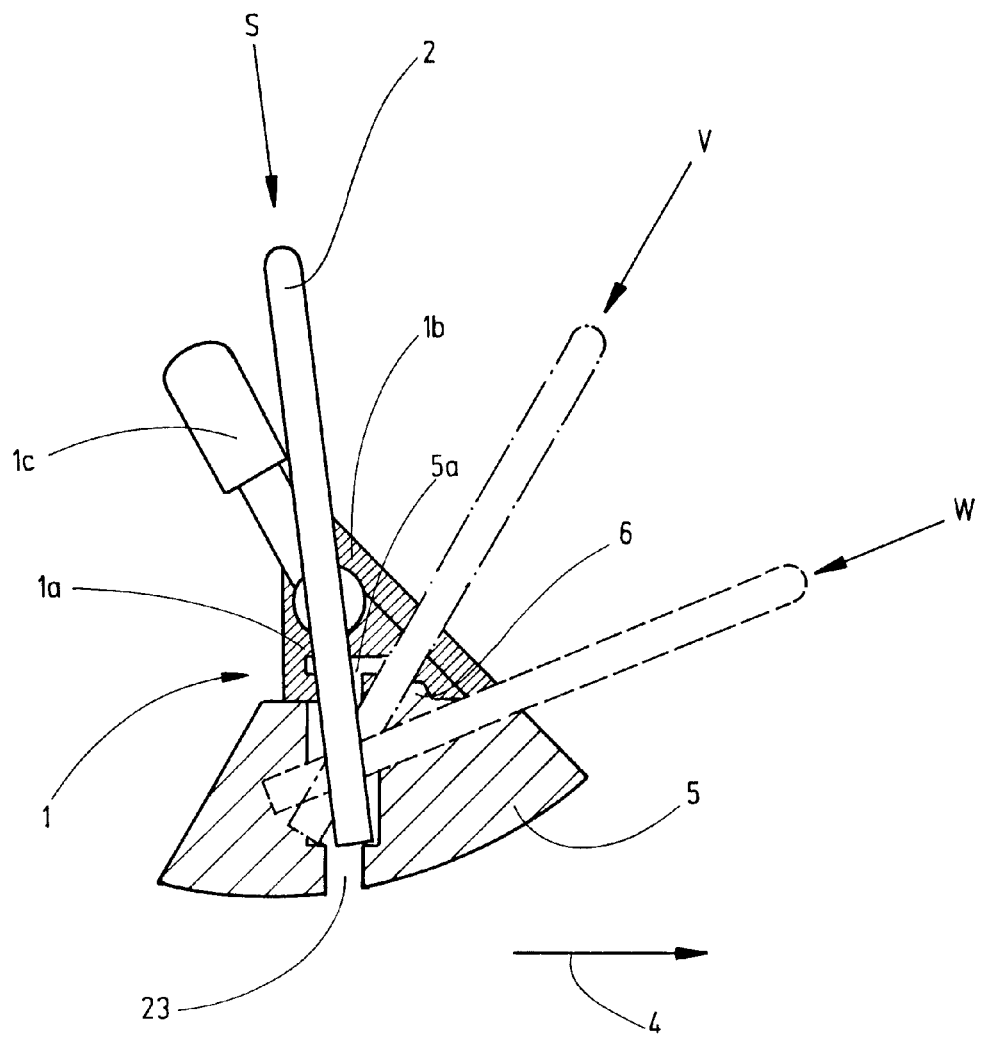
FIG. 2 the blade guard with its three positions in a simplified, partially cut-away side view, FIG. 3 a sectional plan view corresponding to FIG. 1

FIG. 2 shows the three settable positions S, V, W of the blade guard 2 as seen from the side. In section, the drawing shows the segment arc 5, the knife holder 1 with its base body 1a on the guideway 6, the clamping plate 1b and the clamping lever 1c. It also shows the hole 23 for the clamping element 14 (not depicted in this figure) in the segment arc 5 and the slot 5a, T-shaped in this case, in the base body 1a of the knife holder 1 into which the T-shaped head part 15 of the clamping element 14 (both not depicted) engage to press the knife holder 1 against the segment arc 5 when the clamping is engaged accordingly. Due to the disposition of a spring element (not depicted here) underneath the clamping element 14 (also not depicted), for example, a spring or waved washer, more convenient sliding of the knife holder 1 in blade guard position V can be effected. The shoulder in the hole 23 is the supporting surface for such a spring element below the clamping element 14 having a smaller diameter than the region of the clamping element 14.

In the fully raised position, the blade guard 2 is in the protective position S, in which access by the user's hand to the cutting edge 3a of the knife 3 is prevented and, at the same time, the knife holder 1 is fixed in the guideway 6 in its cutting position for controlled sectioning. In the swung-forward central position, the blade guard 2 is in the knife-sliding position V. This permits lateral access to the knife holder 1 and releases fixture of the knife holder 1 so that the latter can be laterally slid on the guideway 6. "Lateral" in this case refers to the viewing angle in FIG. 1. In the third position, swung further downward, the blade guard 2 is in the knife-changing position W, which is also associated with simultaneous fixture of the knife holder 1 in its position on the guideway 6. This permits safe knife changing. It is also possible to initially cut or trim a sample, in cases where (ergonomic) section removal is not important because the sections either fall off of their own accord or can be removed without any caution to avoid damage to the sections because the result is merely waste. However, convenient access with the hand for careful removal of sensitive real sample sections is prevented because the bow of the blade guard obstructs the necessary arm and hand movements.

Figure 3:
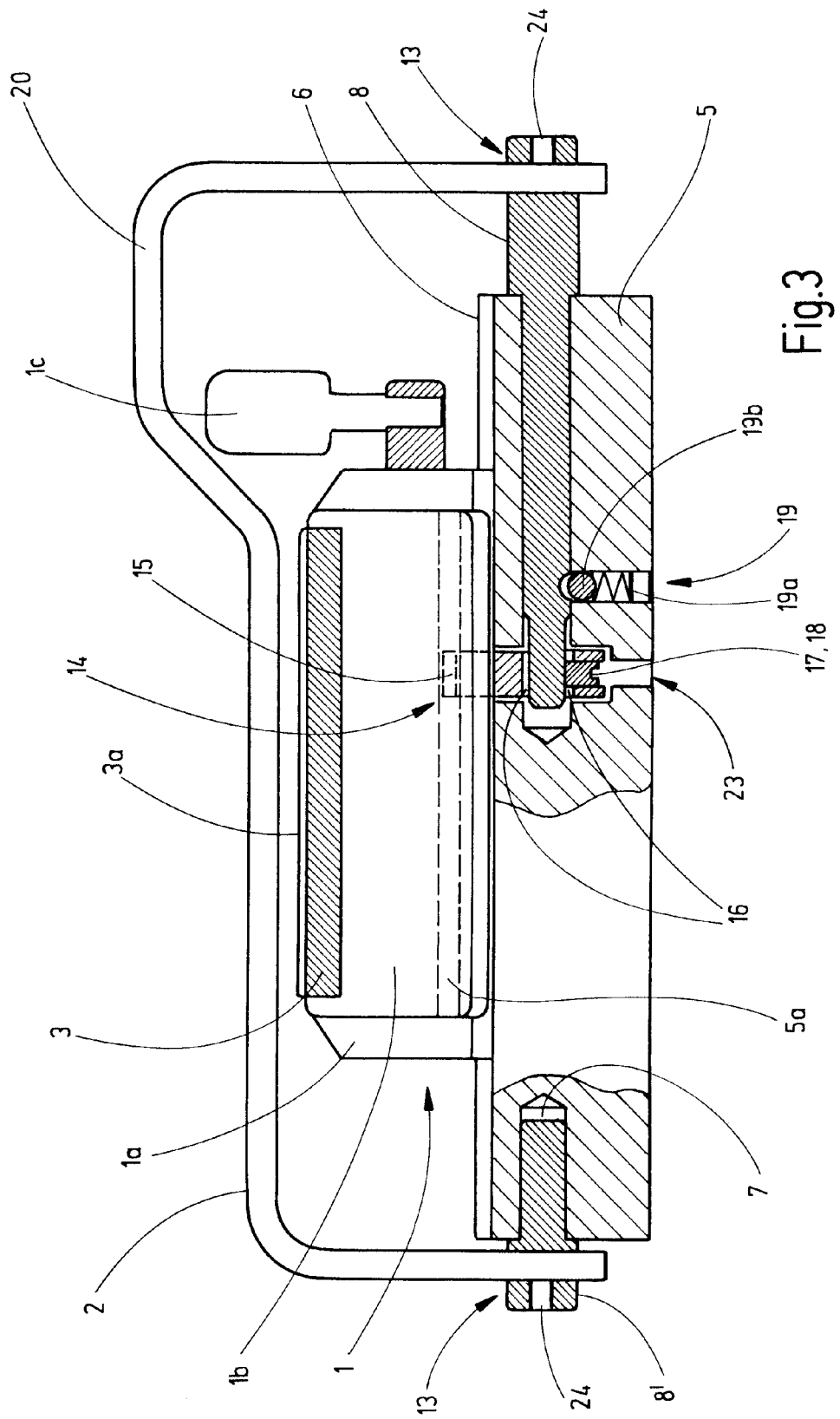

FIG. 3 shows the essential cutaway of FIG. 1 in a plan view with the details of the knife holder 1 already described and further details. Here, too, the figure shows the clamping of the knife 3, wherein the clamped part is shown hatched, while the dangerous cutting edge 3a protrudes over the clamping plate 1b. The blade guard 2 has a single projection 20 here and is constituted by a single component, which ensures good torsional strength. Via the mechanical linkage 13, the blade guard 2 is connected to the shaft 8, 8', which is constituted by two parts in this case. The second part of the shaft 8' provides stabilization for the blade guard 2. Of course, a blade guard 2 with a mechanical linkage 13 on one side only is also conceivable, wherein the shaft 8 can be constituted both by one and two parts. However, a shaft 8 in two parts simplifies mounting of the shaft 8.

The clamping element 14 disposed in the hole 23 of the segment arc 5 is shown in section with hole 16 exposed, showing the shaft 8 extending through the clamping element 14 in the eccentric region 8b. The engagement region 17 is constituted as a set screw 18, such as, for example, a grub screw with a hexagon socket. As a further detail, the latching element 19 is shown as a spring 19a and spring-mounted ball 19b that engages in a recess 11 of the shaft 8. The recess 11 is disposed on the shaft in such a way that it engages when in the knife-sliding position V. In this way, the user feels when he or she has set the position, which means that the knife holder 1 can then be moved laterally in the guideway 6. This position is also held by the latching but can be changed again without effort by the user.

Means are also shown for height adjustment of the bow of the blade guard 2. These are provided in the form of holes in the shaft 8 in the region of the mechanical linkage, within which the blade guard 2 can be freely slid and fixed by means of the locking screws 24. This permits individual adaptation of the freedom of view onto the sample in the protective position S of the blade guard 2. Other practical embodiments of these means are, of course, possible.

Figure 4:
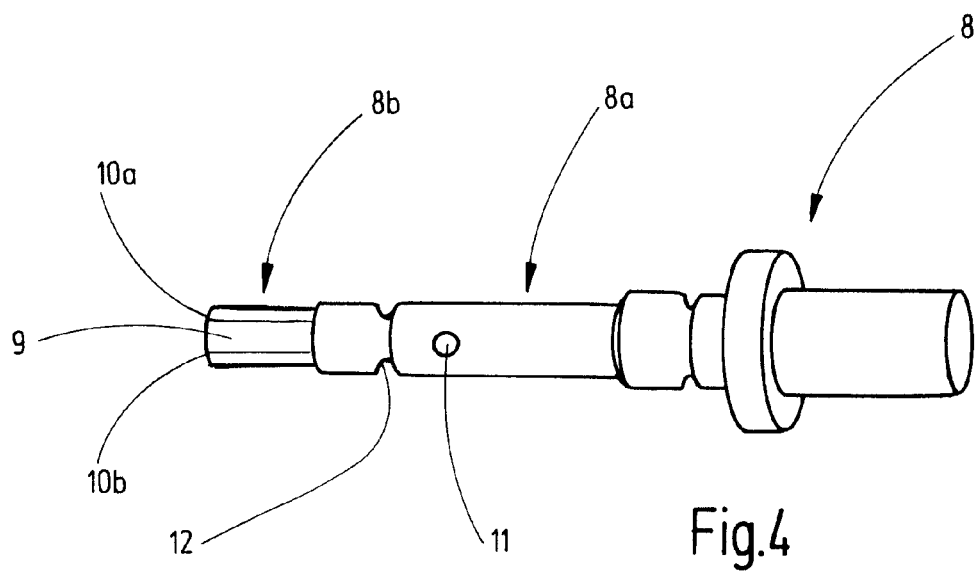
FIG. 4 a plan view of a detail of the inventive shaft.

FIG. 4 shows the shaft 8 in detail. The shaft 8 has a bearing region 8a and an eccentric region 8b. The bearing region 8a is for stable support with as much play as possible in the bearing 7, while the eccentric region 8b, in this case with a smaller diameter than that of the bearing region 8a, is for interaction with the clamping element 14. For this purpose the eccentric region 8b has a flat section 9 in a part of its circumference, wherein the two eccentric clamping keys 10a and 10b are formed by the transitions between the flat section 9 and the circumference of the shaft. The recess 11 is used for engaging the latching element 19 or with its ball 19b to facilitate positioning of the blade guard in the position V. The ring slot 12 is for engagement by the corresponding engagement element to achieve both general securing of the position and stable and reliable axial alignment of the shaft 8 in its bearing 7 with respect to the elements interacting with it, in particular, the clamping element 14 and the latching element 19.

Figure 5:
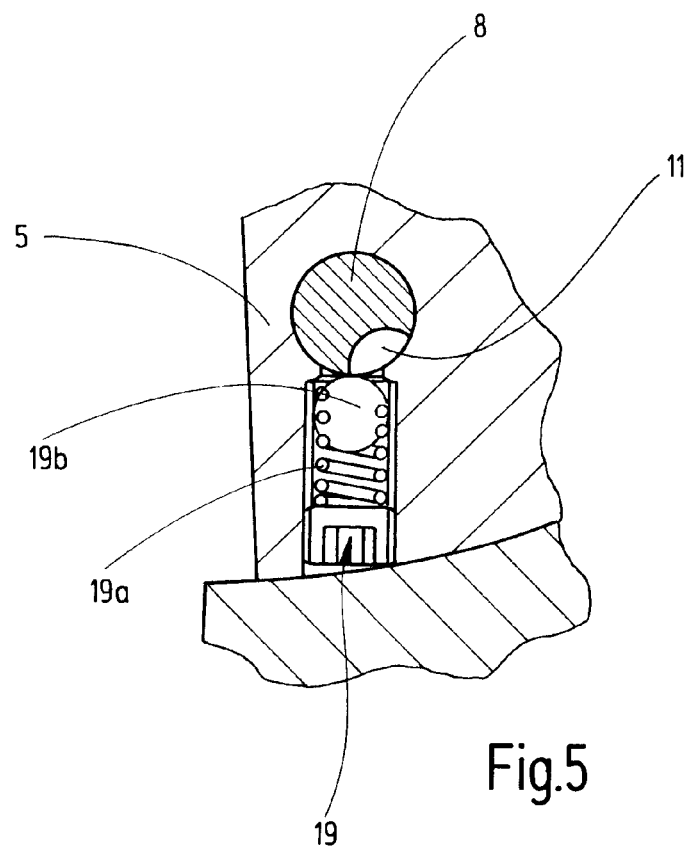
FIG. 5 the latching element in a sectional view as a detail from FIG. 3.

FIG. 5 shows the latching element 19 for FIG. 3 as a detail. The figure clearly shows the spring 19a, against whose spring force a ball 19b is mounted that, when the recess 11 of the shaft 8 is positioned above the ball 19b, latches into the recess 11. Other embodiments of the latching element are, of course, possible. The essential aspect is that the user can easily feel the correct positioning of the blade guard 2 without further pivoting being hindered too much.

Figure 6A:
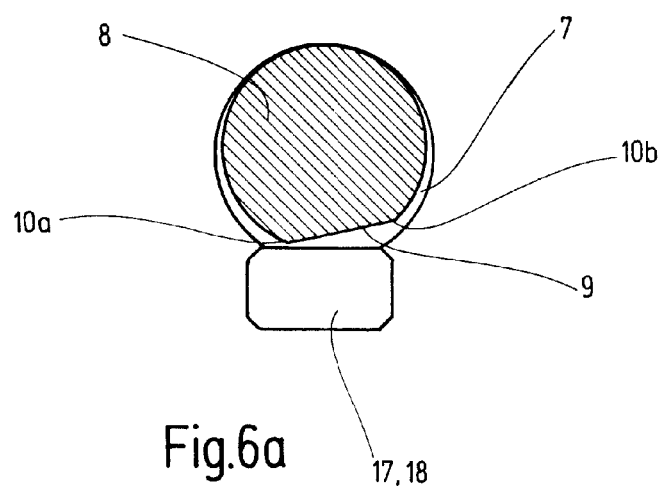
FIGS. 6a,6b,6c schematic sectional detail views of the inventive shaft (eccentric region), FIGS. 7a, 7b an embodiment of the blade guard in a plan view and sectional view and FIG. 8 a further embodiment of the blade guard.
Figure 6B:
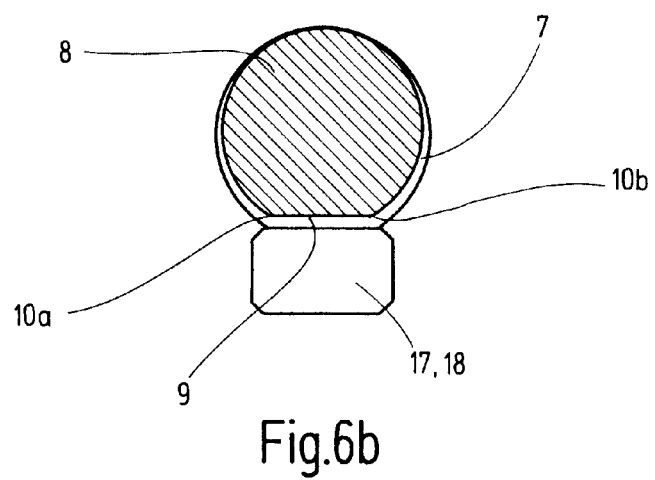
Figure 6C:
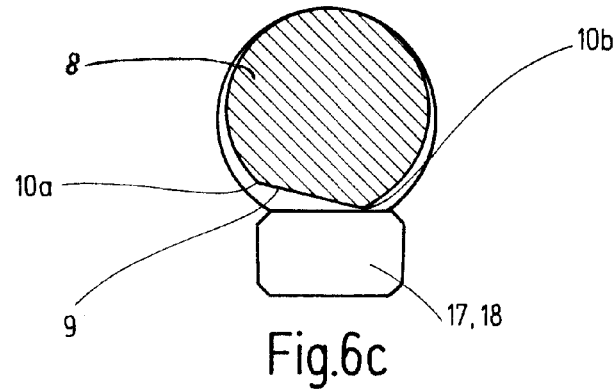

FIGS. 6a, 6b, and 6c show schematic detail views of the shaft 8 in the eccentric region 8b in its bearing 7. The figure clearly shows the flat section 9 and the eccentric clamping keys 10a and 10b that, if the shaft 8 is rotated accordingly—effected by the pivoting movement of the bow of the blade guard 2 via the mechanical linkage 13 (not depicted in this figure)—apply force to the clamping element 14 with the engagement region 17 of the clamping element 14, which presses the latter downward. Because the shaft 8 is constituted with two eccentric clamping keys 10a, 10b and a flat section 9 located between them, two different positions (S and W, see FIGS. 6a and 6c) of the blade guard 2 can be entered in which the knife holder 1 is simultaneously fixed and additionally a third position of the blade guard (V, see FIG. 6b) can be entered in which the knife holder 1 is not fixed. If the engagement region 17, as illustrated schematically here, is constituted, for example, by a set screw 18, the strength of the clamping effect can be freely adjusted, in particular, if this set screw 18 is freely accessible for a tool. This can be achieved simply with a hole 23 in the segment arc 5.

Figure 7A:
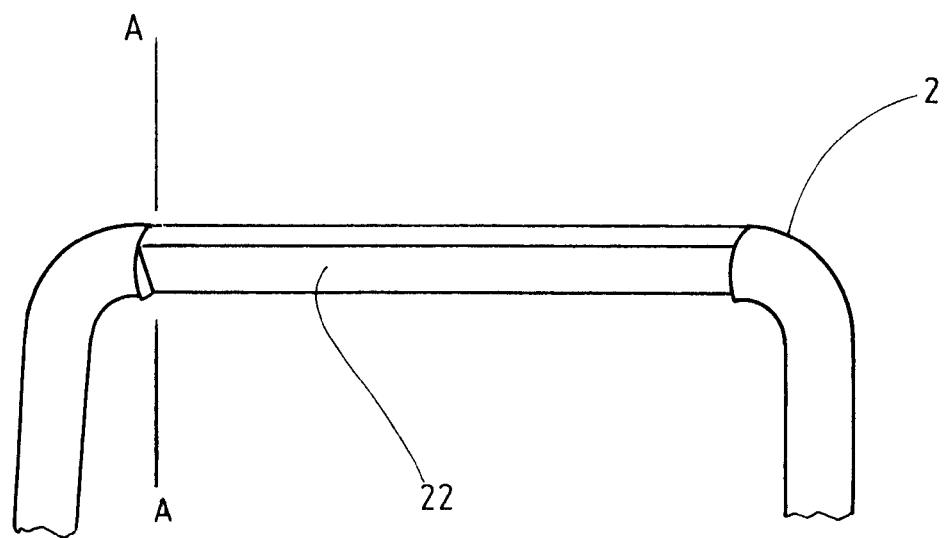
Figure 7B:
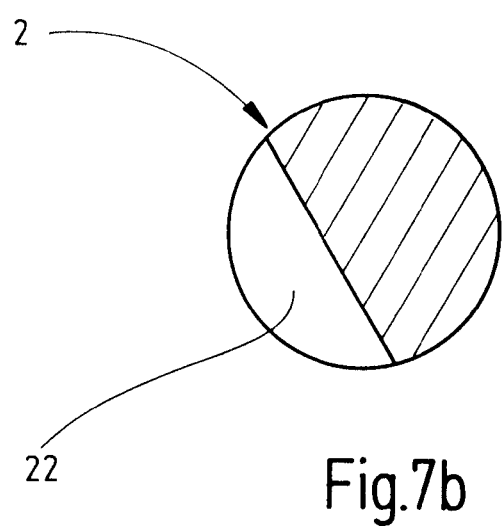

FIGS. 7a and 7b show a special embodiment of the blade guard 2. FIG. 7a shows that the bow of the blade guard 2 has a flat section 22, at least in the region in which it may be located in its protective position S in front of the sample. FIG. 7b shows a section in plane A-A, in which the flat section 22 can be clearly recognized. The effect of this flat section 22 is to enlarge the field of view of the user, who normally looks from the front and above the bow of the blade guard 2 onto the cutting edge 3a and the sample in order to observe and monitor the sectioning operation because the transverse part of the blade guard 2 is in the viewing direction toward the cutting edge 3a, the sample, and the depositing region for the sections. The position and the angle of the flat section 22 with respect to the microtome, on which the knife holder 1 is disposed, can be chosen to suit the application. Suitable dimensions are, for example, a flat section 22 about approx. 2 mm from the diameter at an angle of approx. 25° measured from the work surface. A further improvement of the viewing angle can also be achieved by making the distance of the blade guard 2 from the cutting edge 3a (not depicted in this figure) adjustable (see FIG. 3). This can be achieved, for example, by appropriate means in the mechanical linkage 13 between the blade guard 2 and the shaft 8. Other practical embodiments are, of course, conceivable, e.g. by means of appropriately disposed push/pull connections in the blade guard 2.

Figure 8:
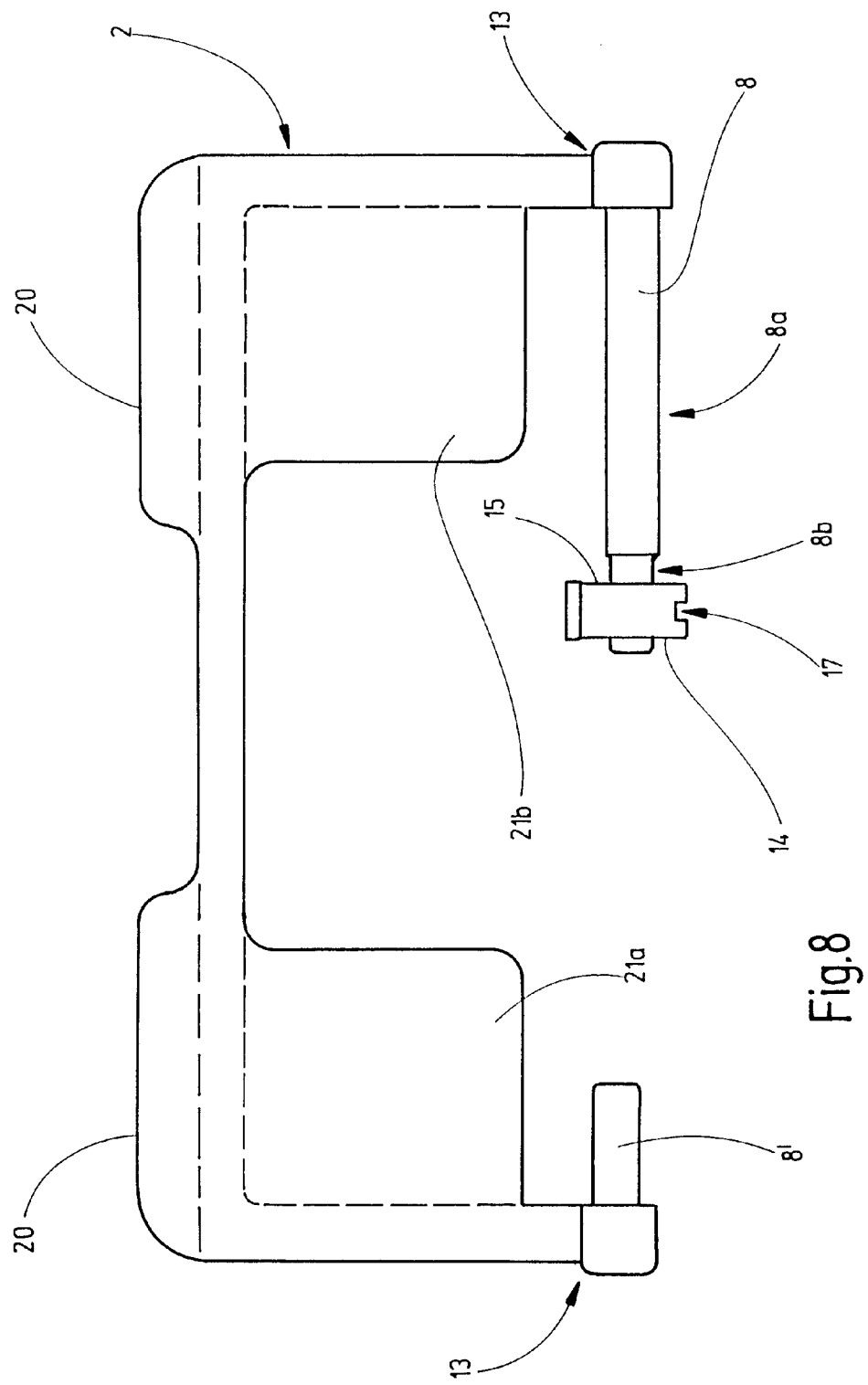

FIG. 8 shows not only the details of the shaft 8 already known with the bearing region 8a and eccentric region 8b and the clamping element 14 shown in a simplified manner with the head part 15 and engagement section 17 but also a further variant of a blade guard 2. This has flat projections 20 and lateral limiting elements 21a, 21b. Of course, such a limiting element 21a or 21b can also be provided on one side only. In any case, the dimensions of the limiting element 21a or 21b must be adapted to the specific requirements. Such a requirement could be that a knife holder 1 should not enter certain positions. It is conceivable to constitute such a limiting element 21a, 21b such that it can be freely slid or positioned on the blade guard 2. In this way, it can be ensured, for example, that certain (already used and therefore no longer useful) parts of the cutting edge 3a are no longer used.

All illustrations are only intended to elucidate the claimed inventive concept based on embodiments. Further embodiments are, of course, possible, in particular, with regard to the type of coupling of the positioning of the blade guard 2 with the fixture of the knife holder 1.

Mechanical means permit very reliable use and, above all, the conversion of common microtomes by the simplest of means. For new devices other couplings are conceivable that, for example, detect the position of the blade guard 2 electronically and also control fixture of the knife holder 1, for example, electronically. But mechanical controls are also conceivable. However, these would be inferior to the direct coupling as described in the claim 2. Fixture of the knife holder 1 itself can be effected by mechanical means, such as clamping fixture, latching, etc. or practically also by means of a solenoid disposed below the knife holder in the segment arc or in the support element 5 of the knife holder 1 and that is energized to effect fixture. Other embodiments of the blade guard 2, in particular, of the projections 20, are also conceivable. A possible and just as effective embodiment as the flat section 22 described in the claim 8 would be to use a transparent material for at least part of the blade guard 2, which is located in the region of the knife holder 1. This material would have to be constituted in such a way as to ensure a sufficiently clear view of the sample and the cutting edge 3a.

LIST OF REFERENCES

1 Knife holder
1a Base body
1b Clamping plate
1c Clamping lever
2 Blade guard
3 Knife 3a Cutting edge
4 Direction of the arrow: side (of the knife) facing away from the sample
5 Support element (e.g. segment arc)
5a Slot (e.g. T-slot)
6 Guideway
7 Bearing
8, 8' Shaft
8a Bearing region
8b Eccentric region
9 Flat section
10a, 10b Eccentric clamping keys
11 Recess
12 Ring slot
13 Mechanical linkage
14 Clamping element
15 Head part
16 Hole
17 Engagement region
18 Set screw
19 Latching element
19a Spring
19b Ball
20 Projection
21a, 21b Limiting element
22 Flat section
23 Hole
24 Locking screws
S Protective position
V Knife-holder-sliding position
W Knife-changing position

I claim:

1. A knife holder device for a rotary microtome, the device comprising:
   a knife holder having a knife, said knife having a cutting edge;
   a blade guard constructed as a pivotable bow, said blade guard having an outer portion extending substantially parallel to said cutting edge;
   a support element, said support element having a guideway in which said knife holder is mounted such that it can be slid and fixed to deploy different regions of the cutting edge during sectioning operation;
   positioning means, said positioning means being constructed to position said outer portion of said blade guard in any of three positions:
   (i) a protective position directly above and closely spaced apart from said cutting edge of said knife, wherein when said blade guard is in said protective position, said positioning means simultaneously fixes said knife holder in said guideway;
   (ii) a knife-holder-sliding position permitting access to said knife holder with simultaneous release of said knife holder in said guideway, wherein, in said knife-holder-sliding position, said outer portion of said blade guard is lowered relative to said protective position; and
   (iii) a knife-changing position permitting free accessibility to said knife holder with simultaneous fixture of said knife holder in said guideway, wherein, in said knife-changing position, said outer portion of said blade guard is lowered relative to said knife-holder-sliding position.

2. The device of claim 1, wherein said positioning means comprises a bearing for receiving a shaft in said support element, a mechanical linkage disposed between said blade guard and said shaft, and a clamping element for fixing said knife holder in said guide way in said protective and said knife-changing positions, wherein said clamping element releases said knife holder in said knife-holder-sliding position.

3. The device of claim 2, wherein said shaft has both a bearing region and an eccentric region with two eccentric clamping keys that are constituted by said shaft having a flat section in said eccentric region in a partial region of the circumference of said shaft, wherein transitions from said circumference to said flat section constitute said two eccentric clamping keys;
   wherein said clamping element has a substantially T-shaped head part for engagement in a correspondingly shaped slot on an underside of said knife holder;
   a hole for receiving said shaft having an engagement region in a lower part of said hole;
   wherein said clamping element is disposed perpendicular to said bearing in such a way that said hole is essentially aligned with said bearing;
   wherein when one of said two eccentric clamping keys engages with said engagement region of said hole, said clamping element is moved downward and fixes said knife holder in said guideway by clamping action of said head part in said slot of the knife holder when said blade guard is in said protective and knife changing positions; and
   wherein a positioning of said flat section in said engagement region at said knife holder sliding position of said blade guard corresponds to the release of said knife holder.

4. The device of claim 2, wherein said shaft has a recess and a latching element is constituted and disposed such that it latches into said recess when said blade guard in said knife-holder-sliding position.

5. The device of claim 4, wherein said latching element comprises a spring and a ball mounted in said spring.

6. The device of claim 2, wherein said shaft has a ring slot and an engagement element that is constituted and disposed such that it engages in said slot and thus secures said shaft against unwanted displacement in said bearing.

7. The device of claim 3, wherein said shaft comprises a first part and a second part which are each connected via a mechanical linkage with said blade guard and are disposed in said bearing, wherein said eccentric region is disposed in said first part of said shaft.

8. The device of claim 1, wherein said blade guard has a flat section on a side facing away from a sample that is dimensioned and disposed such that a user has a free view of the cutting edge of the knife while in said protective position.

9. The device of claim 1, wherein said blade guard has, on a side of a user's hand, a projection as an operating lever for the user's hand.

10. The device of claim 1, wherein said blade guard is constituted by a single component.

11. The device of claim 1, wherein said blade guard has, inside said bow of said blade guard, a laterally disposed limiting element that, in said protective position, is located to a left and/or right of said knife holder so that a lateral limitation is set for positioning of said knife holder in said guideway during sectioning operation.

* * * * *